US009251994B2

(12) United States Patent
Watanabe et al.

(10) Patent No.: US 9,251,994 B2
(45) Date of Patent: Feb. 2, 2016

(54) X-RAY TUBE ASSEMBLY AND X-RAY COMPUTERIZED TOMOGRAPHY SCANNER

(71) Applicants: KABUSHIKI KAISHA TOSHIBA, Minato-ku (JP); Toshiba Electron Tubes & Devices Co., Ltd., Otawara-shi (JP)

(72) Inventors: Miki Watanabe, Sakura (JP); Tomonari Ishihara, Otawara (JP); Hidero Anno, Otawara (JP); Hideki Ide, Otawara (JP)

(73) Assignees: KABUSHIKI KAISHA TOSHIBA, Minato-ku (JP); Toshiba Electron Tubes & Devices Co., Ltd., Otawara-shi (JP)

( * ) Notice: Subject to any disclaimer, the term of this patent is extended or adjusted under 35 U.S.C. 154(b) by 113 days.

(21) Appl. No.: 14/249,741

(22) Filed: Apr. 10, 2014

(65) Prior Publication Data

US 2014/0314197 A1    Oct. 23, 2014

(30) Foreign Application Priority Data

Apr. 18, 2013    (JP) .................................. 2013-087379

(51) Int. Cl.
| | |
|---|---|
| *H01J 35/10* | (2006.01) |
| *H01J 35/12* | (2006.01) |
| *A61B 6/03* | (2006.01) |
| *A61B 6/00* | (2006.01) |

(52) U.S. Cl.
CPC ................. *H01J 35/12* (2013.01); *A61B 6/032* (2013.01); *A61B 6/4488* (2013.01)

(58) Field of Classification Search
CPC ....... H01J 35/12; H01J 35/105; H01J 35/106; H01J 2235/1204; H01J 2235/1216; H01J 2235/1262; A61B 6/4488; H05G 1/025
USPC .............................. 378/4, 130, 141, 199, 200
See application file for complete search history.

(56) References Cited

U.S. PATENT DOCUMENTS 6,491,428 B1 *   12/2002   Takanashi .............. A61B 6/035
                                                   378/199

FOREIGN PATENT DOCUMENTS

| JP | 9-56710 | 3/1997 |
|---|---|---|
| JP | 2001-137224 | 5/2001 |
| JP | 2007-514287 | 5/2007 |
| WO | WO 2005/057991 A1 | 6/2005 |

\* cited by examiner

*Primary Examiner* — Jurie Yun
(74) *Attorney, Agent, or Firm* — Oblon, McClelland, Maier & Neustadt, L.L.P.

(57) ABSTRACT

According to one embodiment, an X-ray tube assembly includes a housing, an X-ray tube, a coolant to which at least a part of heat generated by the X-ray tube is transferred, a circulation channel through which the coolant is circulated, a circulation pump, a radiator, an air filter and a fan unit. The air filter is formed of a three-dimensional nonwoven fabric that is formed of irregularly tangled resin fibers and provides a three-dimensional structure having a spatial volume ratio of not less than 93%. The air filter permits air to pass therethrough to eliminate dust from the air.

15 Claims, 13 Drawing Sheets

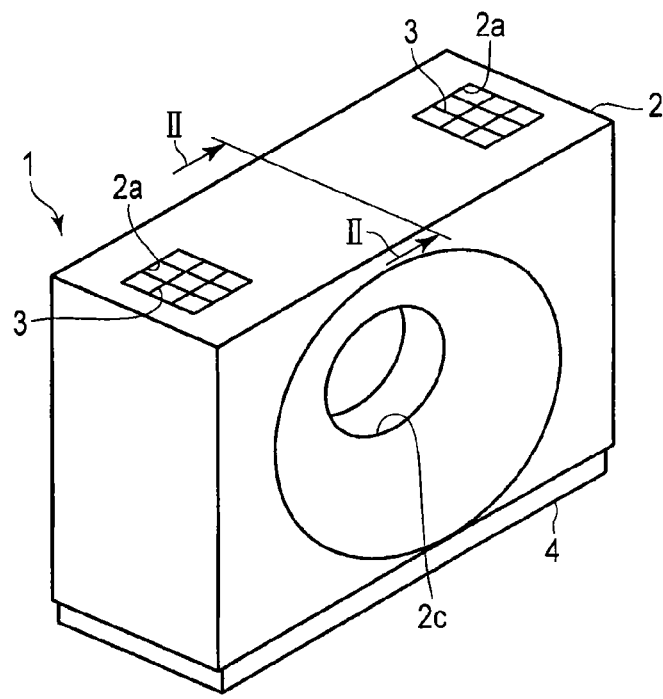
F I G. 1
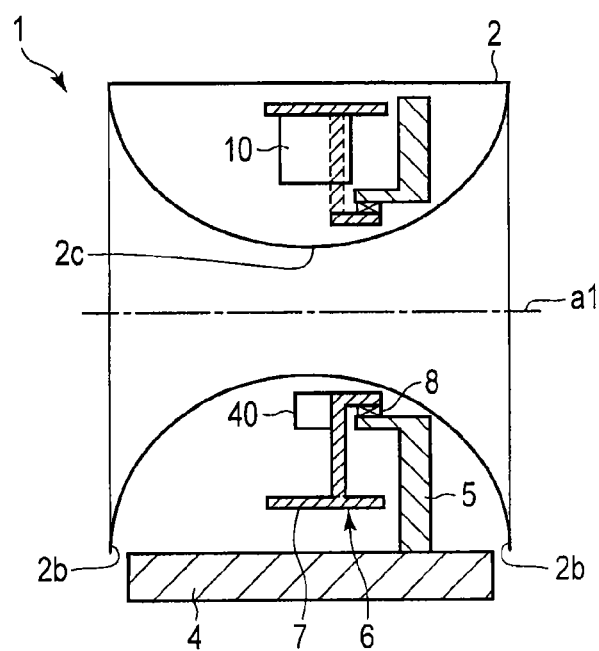
F I G. 2

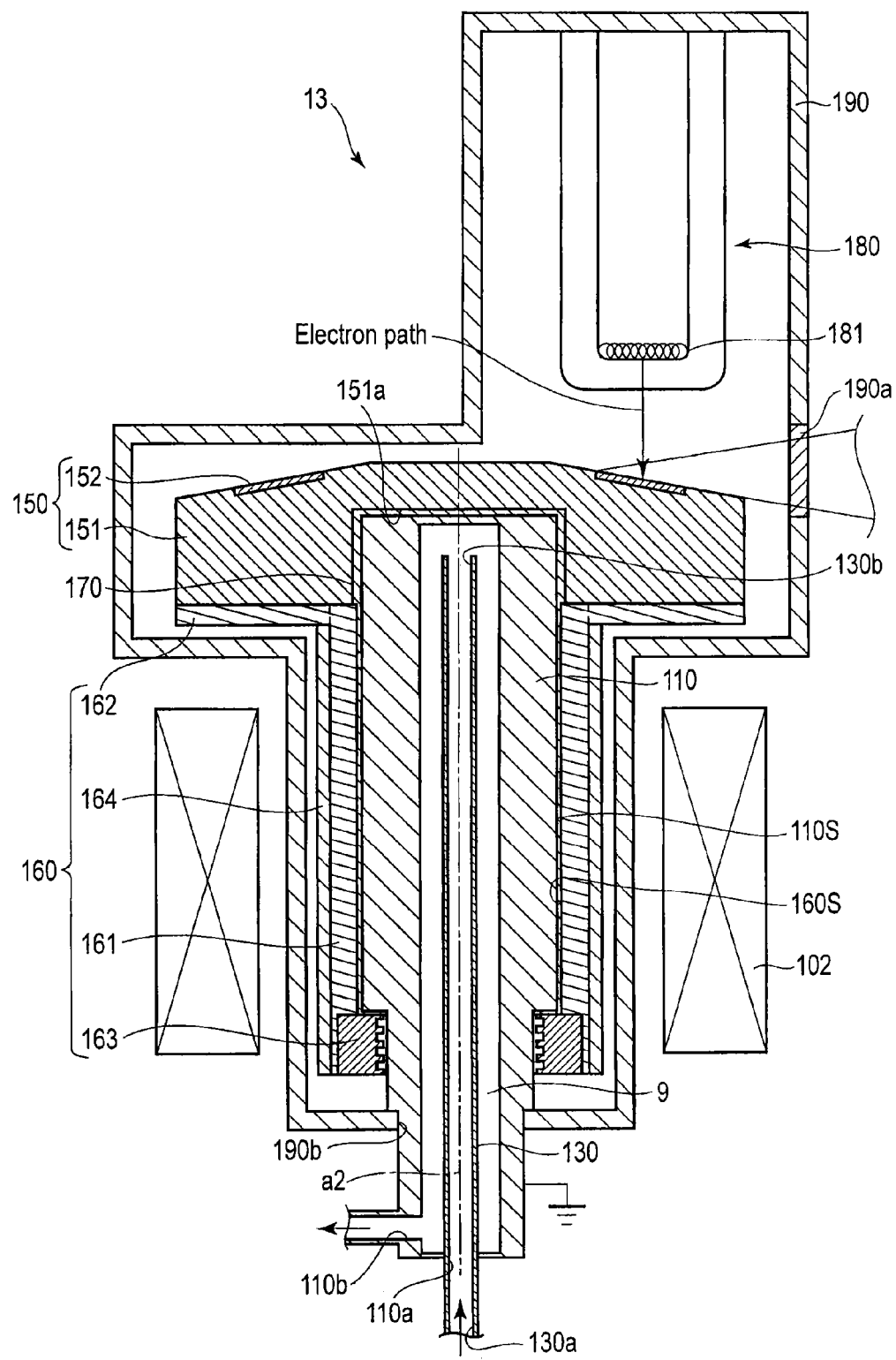
F I G. 6

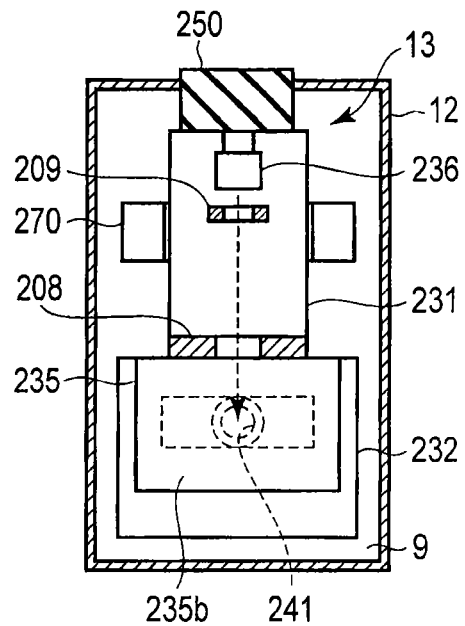
F I G. 7
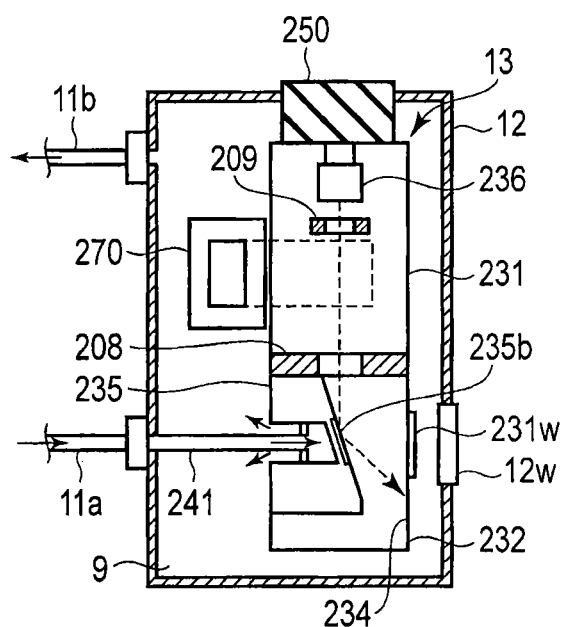
F I G. 8

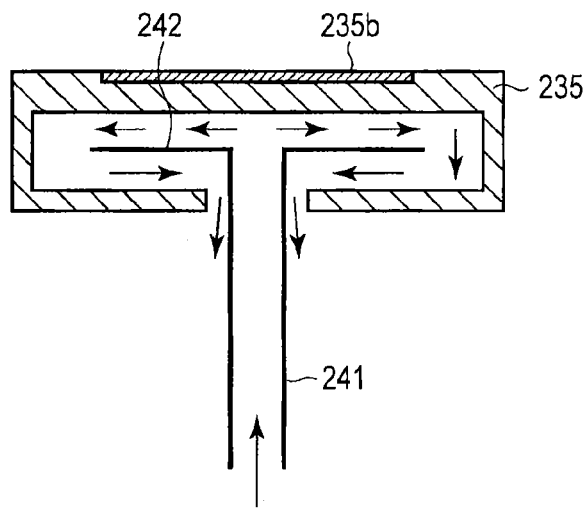
F I G. 9
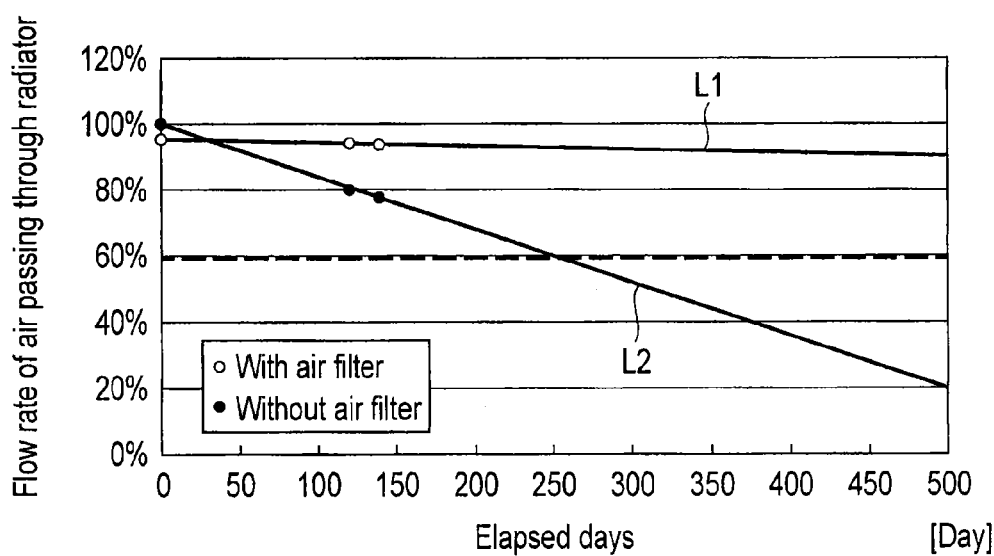
F I G. 10

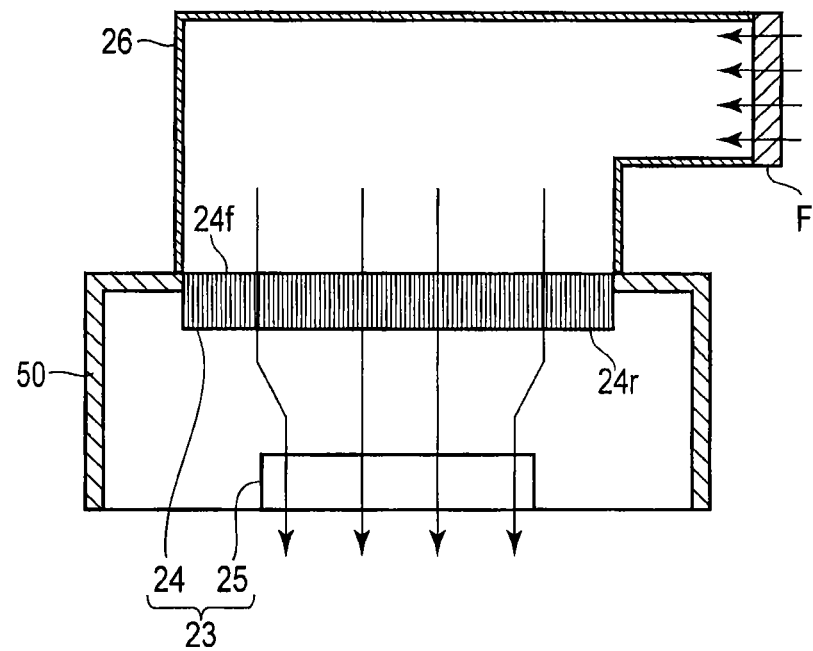
F I G. 15
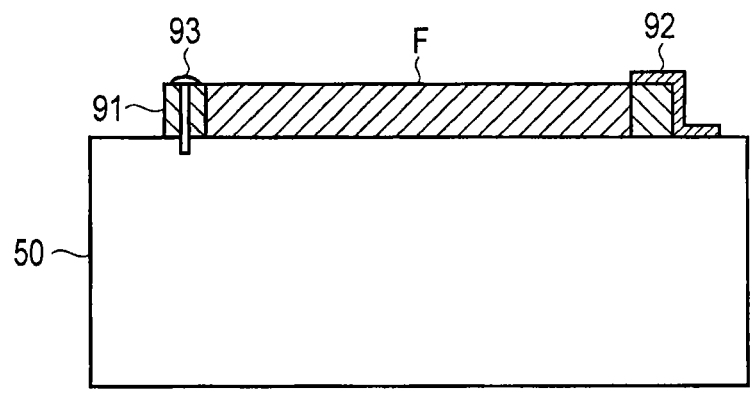
F I G. 16

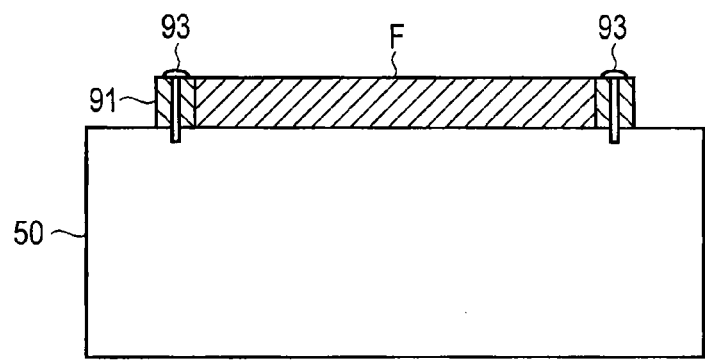
F I G. 17
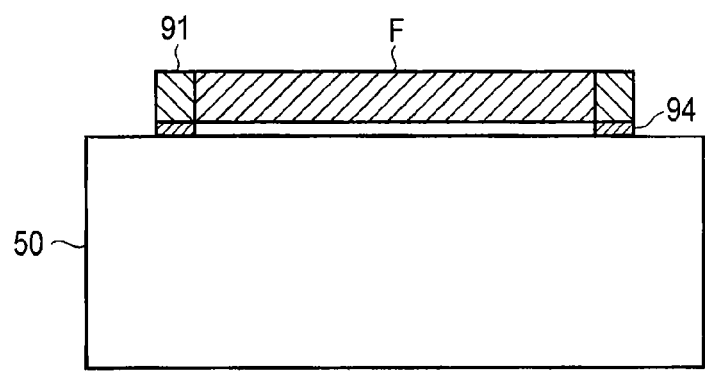
F I G. 18
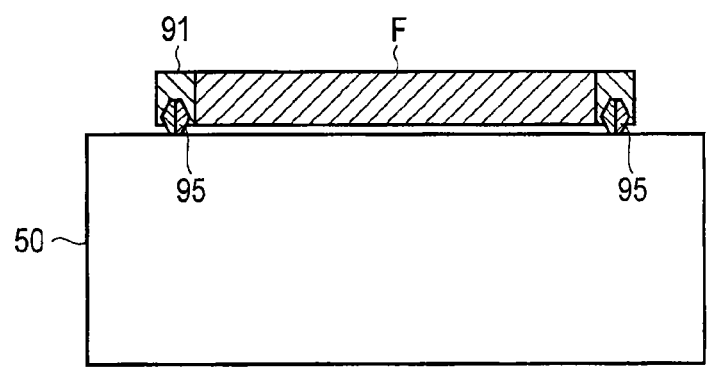
F I G. 19

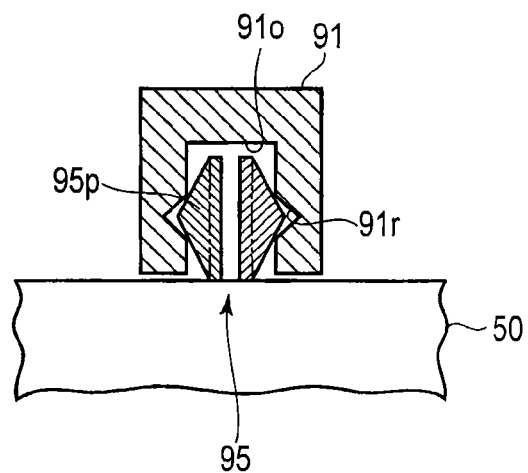
F I G. 20
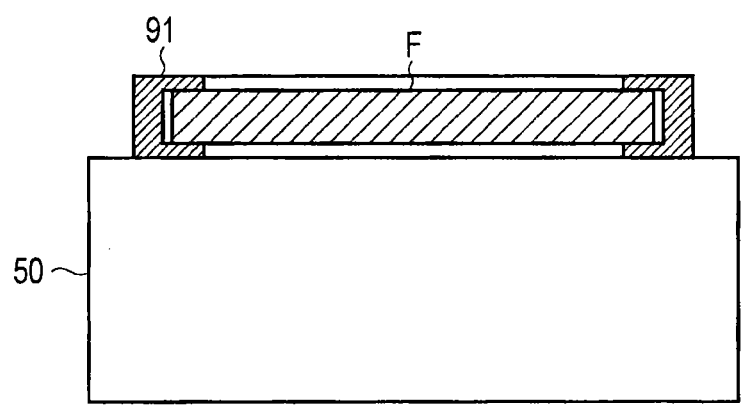
F I G. 21
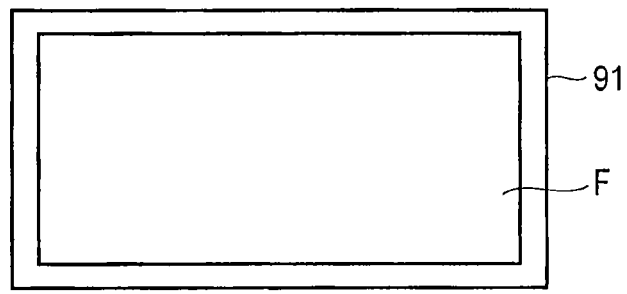
F I G. 22

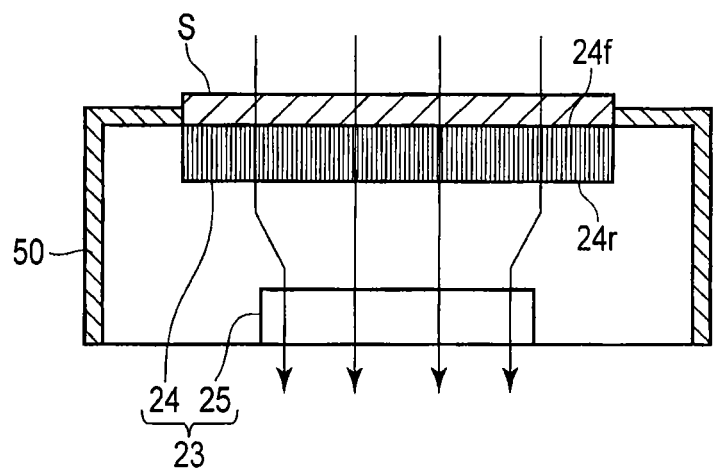
F I G. 26

X-RAY TUBE ASSEMBLY AND X-RAY COMPUTERIZED TOMOGRAPHY SCANNER

CROSS-REFERENCE TO RELATED APPLICATIONS

This application is based upon and claims the benefit of priority from Japanese Patent Application No. 2013-087379, filed Apr. 18, 2013, the entire contents of which are incorporated herein by reference.

FIELD

Embodiments described herein relate generally to an X-ray tube assembly and an X-ray computerized tomography scanner.

BACKGROUND

The gantry of an X-ray computerized tomography scanner (hereinafter referred to as an X-ray CT scanner) comprises a stationary frame, a rotating frame rotatably supported by the stationary frame, and a housing containing the stationary frame and the rotating frame. The gantry also comprises an X-ray tube assembly mounted on the rotating frame, an X-ray detector, a cooling unit (cooler), etc.

More specifically, the rotating frame has a ring-shaped frame member, and the X-ray tube assembly, the X-ray detector and the cooling unit are attached to the inner wall of the ring-shaped frame member. These components are heavy and hence impart significant pressure against the installation surface, although they are relatively compact. Therefore, the components are secured to the installation surface by an especially strong anchoring force.

The strong anchoring of the X-ray tube assembly and the cooling unit can be maintained even when the rotating frame is rotated at high speed to thereby exert a significant centrifugal force upon the X-ray tube assembly and the cooling unit.

The X-ray tube assembly and the cooling unit are connected to each other via a circulation channel for circulating a coolant used to transmit the heat generated by an X-ray tube. The exothermic source of the X-ray CT scanner is the X-ray tube. The heat generated by the X-ray tube is transmitted to the coolant, and the thus-heated coolant is guided into the cooling unit. The cooling unit includes a radiator and a fan unit. The coolant cooled by the coolant unit is returned to the X-ray tube.

BRIEF DESCRIPTION OF THE DRAWINGS

FIG. 1 is a perspective view showing the appearance of the gantry of an X-ray CT scanner according to a first embodiment;

FIG. 2 is a cross-sectional view illustrating the X-ray CT scanner taken along line II-II in FIG. 1;

FIG. 6 is a cross-sectional view showing an X-ray tube assembly according to Example 1 and incorporated in the X-ray CT scanner of the first embodiment;

FIG. 7 is a cross-sectional view showing an X-ray tube assembly according to Example 2 and incorporated in the X-ray CT scanner of the first embodiment;

FIG. 8 is another cross-sectional view of the X-ray tube assembly shown in FIG. 7;

FIG. 9 is a partly enlarged cross-sectional view of the X-ray tube assemblies shown in FIGS. 7 and 8;

FIG. 10 is a graph showing variations with elapsed days in the flow rates of the air passing through the radiators of the X-ray CT scanner of the first embodiment and that of Comparative Example 1;

FIG. 15 is a schematic cross-sectional view showing a part of a cooling unit incorporated in an X-ray CT scanner according to a fourth embodiment;

FIG. 16 is a schematic cross-sectional view showing a part of a cooling unit incorporated in an X-ray CT scanner according to a fifth embodiment, showing an example of installation of an air filter;

FIG. 17 is a schematic cross-sectional view showing a part of a cooling unit incorporated in an X-ray CT scanner according to a modification of the fifth embodiment, showing an example of installation of an air filter;

FIG. 18 is a schematic cross-sectional view showing a part of a cooling unit incorporated in an X-ray CT scanner according to another modification of the fifth embodiment, showing an example of installation of an air filter;

FIG. 19 is a schematic cross-sectional view showing a part of a cooling unit incorporated in an X-ray CT scanner according to yet another modification of the fifth embodiment, showing an example of installation of an air filter;

FIG. 20 is an enlarged cross-sectional view showing a part of the cooling unit of FIG. 19, showing a frame member and projections;

FIG. 21 is a schematic cross-sectional view showing a part of a cooling unit incorporated in an X-ray CT scanner according to a further modification of the fifth embodiment, showing an example of installation of an air filter;

FIG. 22 is a top view of the air filter and the frame member shown in FIG. 21;

FIG. 26 is a schematic cross-sectional view showing a part of a cooling unit incorporated in the X-ray CT scanner of Comparative Example 3.

DETAILED DESCRIPTION

In general, according to one embodiment, there is provided an X-ray tube assembly comprising: a housing; an X-ray tube housed in the housing and including a cathode configured to emit an electron beam, an anode target configured to discharge an X ray when the electron beam is applied to the anode target, and a vacuum envelope containing the cathode and the anode target; a coolant to which at least a part of heat generated by the X-ray tube is transferred; a circulation channel through which the coolant is circulated; a circulation pump provided across the circulation channel and configured to circulate the coolant; a radiator of a fin-tube type provided across the circulation channel and configured to discharge the heat of the coolant to an outside; an air filter formed of a three-dimensional nonwoven fabric and configured to permit air to pass therethrough to eliminate dust from the air, the three-dimensional nonwoven fabric being formed of irregularly tangled resin fiber and providing a three-dimensional structure having a spatial volume ratio of not less than 93%; and a fan unit configured to create a flow of air passing through the radiator after passing through the air filter.

According to another embodiment, there is provided an X-ray computerized tomography scanner comprising: an X-ray tube assembly including: a housing; an X-ray tube housed in the housing and including a cathode configured to emit an electron beam, an anode target configured to discharge an X ray when the electron beam is applied to the anode target, and a vacuum envelope containing the cathode and the anode target; a coolant to which at least a part of heat generated by the X-ray tube is transferred; a circulation channel through which the coolant is circulated; a circulation pump provided across the circulation channel and configured to circulate the coolant; a radiator of a fin-tube type provided across the circulation channel and configured to discharge the heat of the coolant to an outside; an air filter formed of a three-dimensional nonwoven fabric and configured to permit air to pass therethrough to eliminate dust from the air, the three-dimensional nonwoven fabric being formed of irregularly tangled resin fiber and providing a three-dimensional structure having a spatial volume ratio of not less than 93%; and a fan unit configured to create a flow of air passing through the radiator after passing through the air filter; and an X-ray detector configured to detect the X ray; and a rotating frame to which the X-ray tube assembly and the X-ray detector are attached, the air filter being exposed to the space within the inner wall of the frame member.

Referring now to the accompanying drawings, an X-ray computerized tomography scanner according to a first embodiment will be described in detail. The X-ray computerized tomography scanner will hereinafter be referred to as an X-ray CT scanner.

Figure 3:
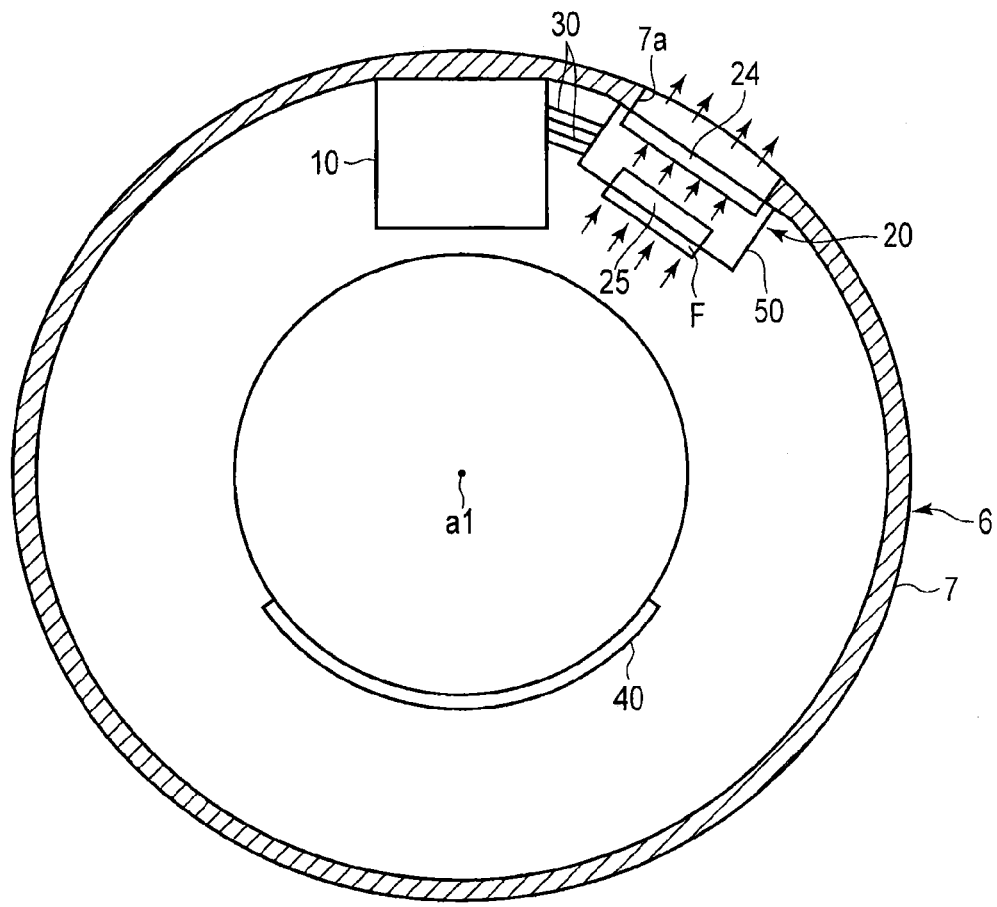
FIG. 3 is a front view showing the rotating frame of FIG. 2, and an X-ray tube assembly, a cooling unit and an X-ray detector mounted on the rotating frame.

FIG. 1 is a perspective view showing the appearance of the gantry of an X-ray CT scanner according to the first embodiment. FIG. 2 is a cross-sectional view illustrating the X-ray CT scanner taken along line II-II in FIG. 1. FIG. 3 is a front view of the rotating frame shown in FIG. 2, and an X-ray tube assembly, a cooling unit and an X-ray detector mounted on the rotating frame.

As shown in FIGS. 1 to 3, an X-ray CT scanner 1 comprises a housing 2, a base 4, a stationary frame 5, a rotating frame 6, a bearing member 8, an X-ray tube assembly 10, a cooling unit 20 and an X-ray detector 40.

The housing 2 contains a number of components as mentioned above. The housing 2 provides the outer appearance of the X-ray CT scanner 1. The housing 2 includes exhaust ports 2a, suction ports 2b and an introduction port 2c.

The exhaust ports 2a are formed in the upper portion of the housing 2, and are covered with mesh covers 3 of a high ventilation property. The X-ray CT scanner 1 further comprises a fan unit (not shown) contained in the housing 2 and opposing the cover 3. As a result, the air in the housing 2 can be exhausted to the outside of the housing 2 through the exhaust ports 2a.

The suction ports 2b are formed in the lower portion of the housing 2. In this embodiment, the suction ports 2b are formed between the housing 2 and the base 4. Through the suction ports 2b, outside fresh air can be introduced into the housing 2.

Since the air in the housing 2 can be exchanged with the outside air as described above, increases in the temperature of the inside air can be suppressed.

The introduction port 2c is used to introduce a test subject into the scanner. The X-ray CT scanner 1 also comprises a bed (not shown) for the test subject.

The stationary frame 5 is fixed to the base 4. The bearing (ball/roll bearing) member 8 functioning as a bearing mechanism is provided between the stationary frame 5 and the rotating frame 6.

The rotating frame 6 is rotatably supported by the stationary frame 5 via the bearing member 8. The rotating frame 6 is called a gantry, and is rotatable about its rotation axis (gantry center) a1. To rotate the rotating frame 6 at high speed, the X-ray CT scanner employs, for example, a direct drive motor.

The rotating frame 6 has a ring-shaped frame member 7 positioned at the outermost peripheral portion of the frame. The frame member 7 has at least one opening 7a. The number of openings 7a and the size of each opening 7a can be made to correspond to those of fan units 25 described later.

The X-ray tube assembly 10, the cooling unit 20 and the X-ray detector 40 are attached to the rotating frame 6. The X-ray tube assembly 10 and the cooling unit 20 are secured to the inner wall of the frame member 7. A high-voltage generating source (not shown) may also be secured to the inner wall of the frame member 7.

The X-ray tube assembly 10 and the cooling unit 20 are great in mass, although they are relatively compact in size. Therefore, their installation surfaces are highly pressurized, whereby those components are strongly fixed to the frame member 7. As a result, even when the rotating frame 6 is rotated at high speed and hence a large centrifugal force is exerted on the X-ray tube assembly 10 and the cooling unit 20, their strong fixing to the frame member 7 is maintained.

The X-ray tube assembly 10 functions as an X-ray generator and generates X rays. The X-ray detector 40 opposes the X-ray tube assembly (X-ray tube) 10 with the rotation axis a1 interposed therebetween. The X-ray detector 40 has a plurality of X-ray detection elements arranged in, for example, an arc. The X-ray CT scanner 1 may employ a plurality of X-ray detectors 40. The X-ray detector(s) 40 detects an X ray emitted from the X-ray tube assembly 10 and passing through the test subject, and converts the detected X ray into an electric signal.

The X-ray CT scanner 1 may also comprise a data collecting device (not shown) attached to the rotating frame 6 and configured to amplify the electric signal output from the X-ray detector 40 and AD convert the signal. Further, a device (not shown) configured to apply power, a control signal, etc., to the X-ray assembly 10, the cooling unit 20, etc., may be incorporated in the stationary frame 5. The power and the control signal can be supplied to the X-ray assembly 10, the cooling unit 20, etc., attached to the rotating frame 6 via a slip ring.

When the X-ray CT scanner 1 is in an operation state, the rotating frame 6 rotates about the rotation axis a1. At this time, the X-ray assembly 10, the cooling unit 20, the X-ray detector 40, etc., rotate around the test subject along with the rotating frame 6, whereby an X ray is emitted from the X-ray tube assembly 10.

The X-ray passes through the test subject and reaches the X-ray detector 40, where the intensity of the X ray is detected. For example, the detection signal from the X-ray detector 40 is amplified the above-mentioned data collecting device, and A/D converted into a digital signal, and is sent via a slip ring to a computer (not shown).

The computer calculates an X-ray absorption factor in an area of interest of the test subject, based on the digital detection signal, and generates image data for generating a tomogram of the test subject, based on the calculation result. The image data is sent to, for example, a display apparatus (not shown), where a tomogram corresponding to the image data is displayed on the screen.

As described above, in the X-ray CT scanner 1, the X-ray assembly 10 and the X-ray detector 40 are rotated with the test subject held therebetween, whereby so-called projection data is obtained, which corresponds to the X rays of different intensities returned from an area of a certain angle, such as 360°, included in a scanned cross section of the test subject. Based on this projection data, a tomogram is generated by a predetermined data reconstructing program.

Figure 4:
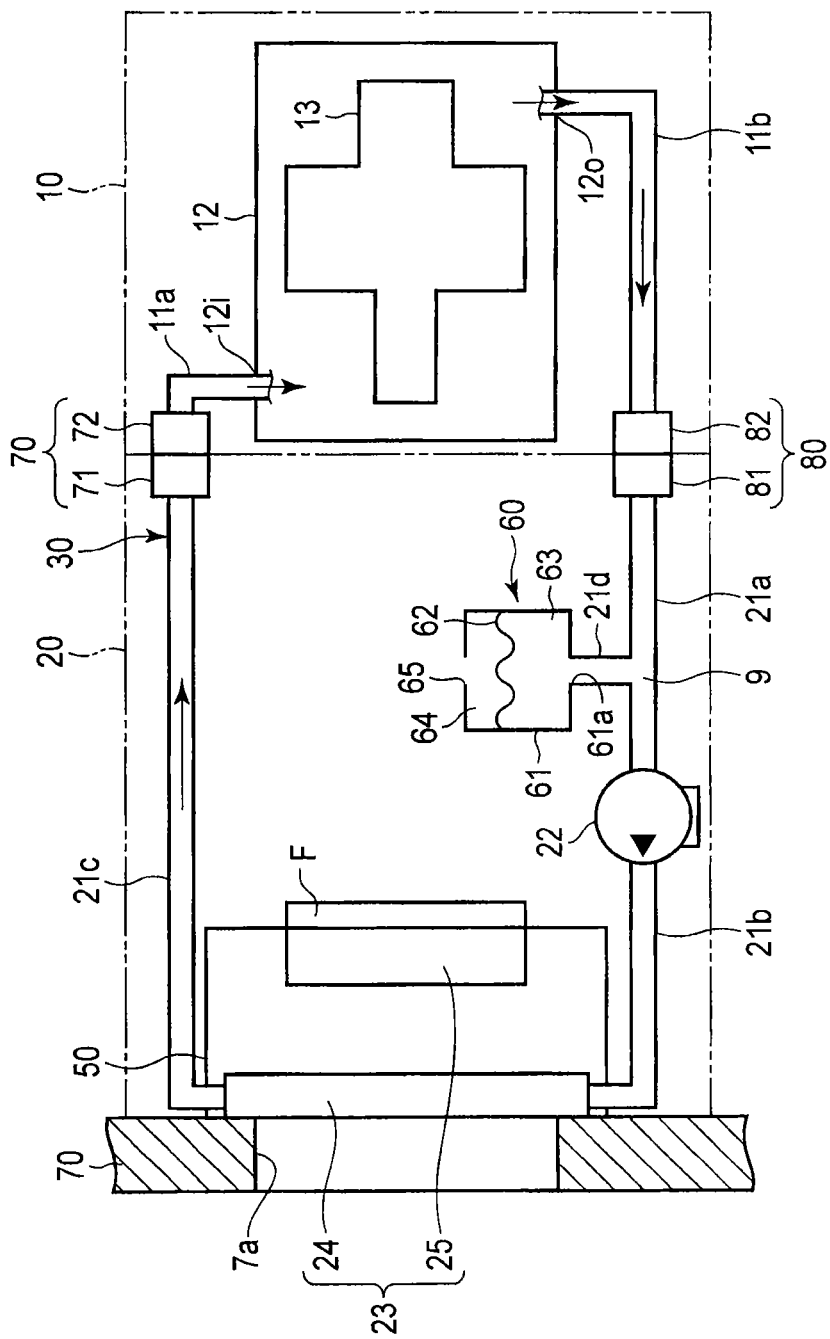
FIG. 4 is a schematic view showing the X-ray tube assembly and the cooling unit.

FIG. 4 is a schematic view showing the X-ray tube assembly 10 and the cooling unit 20. In this figure, the positional relationship between the opening 7a and a heat exchanger 23, described later, is emphasized.

As shown in FIGS. 3 and 4, the X-ray tube assembly 10 comprises a housing 12 and an X-ray tube 13 contained therein. The housing 12 (X-ray tube assembly 10) is directly or indirectly secured to the rotating frame 6 independently. In this embodiment, the housing 12 is directly secured to the inner wall of the frame member 7.

The X-ray tube 13 comprises a cathode configured to emit electron beams, an anode target configured to emit X rays when receiving electron beams, and a vacuum envelope containing the cathode and the anode target. The X-ray CT scanner 1 comprises a coolant 9, to which at least part of the heat generated by the X-ray tube 13 is transferred.

The X-ray tube assembly 10 includes a conduit 11a and a conduit 11b. The conduit 11a has an end air-tightly attached to a coolant inlet 12i incorporated in the housing 12, and the other end air-tightly attached to a socket 72. The conduit 11b has an end air-tightly attached to a coolant outlet 12o incorporated in the housing 12, and the other end air-tightly attached to a socket 82. The conduits 11a and 11b provide part of a circulation channel 30 through which the coolant 9 circulates.

When the heat transfer surface is the outer surface of the X-ray tube 13, the coolant 9 is contained in the housing 12. The housing 12 forms a part of the circulation channel 30 along with the conduits 11a and 11b. When the coolant 9 circulates the heat transfer surface of the X-ray tube 13, the X-ray tube 13, in particular, an anode target, described later, is cooled.

When the heat transfer surface is positioned inside the X-ray tube 13, the conduit 11a and the X-ray tube 13 are directly or indirectly (via a coupling member) connected to each other, or the conduit 11b and the X-ray tube 13 are directly or indirectly (via a coupling member) connected to each other. The insides of the housing 12 and the X-ray tube 13 form part of the circulation channel 30 along with the conduits 11a and 11b. As a result, when the coolant 9 circulates on the heat transfer surface within the X-ray tube 13, the X-ray tube 13, in particular, the anode target, described later, is cooled.

Further, when the heat transfer surface is positioned within the X-ray tube 13 and the conduits 11a and 11b are coupled to the X-ray tube 13, coolant may be or may not be contained in the housing 12. In this case, a coolant different from the coolant 9 may be contained in the housing 12. The interior of the X-ray tube 13 forms part of the circulation channel 30 along with the conduits 11a and 11b. As a result, when the coolant 9 circulates on the heat transfer surface within the X-ray tube 13, the X-ray tube 13, in particular, the anode target, described later, is cooled.

The cooling unit 20 comprises conduits 21a, 21b, 21c and 21d, a circulation pump 22, the above-mentioned heat exchanger 23, and a bellows mechanism 60. The conduit 21a has an end air-tightly attached to a plug 81. The conduit 21c has an end air-tightly attached to a plug 71. The conduit 21d has an end air-tightly attached to the conduit 21a. The conduits 21a, 21b, 21c and 21d form part of the circulation channel 30.

The circulation pump 22 is directly or indirectly secured to the inner wall of the frame member 7 independently. In this embodiment, the circulation pump 22 is directly secured to the inner wall of the frame member 7. The circulation pump 22 is provided across the circulation channel 30. In the embodiment, the circulation pump 22 is air-tightly interposed between the conduits 21a and 12b. The circulation pump 22 discharges the coolant 9 to the conduit 21b and receives the coolant 9 through the conduit 21a. The circulation pump 22 can circulate the coolant 9 through the circulation channel 30.

Figure 5:
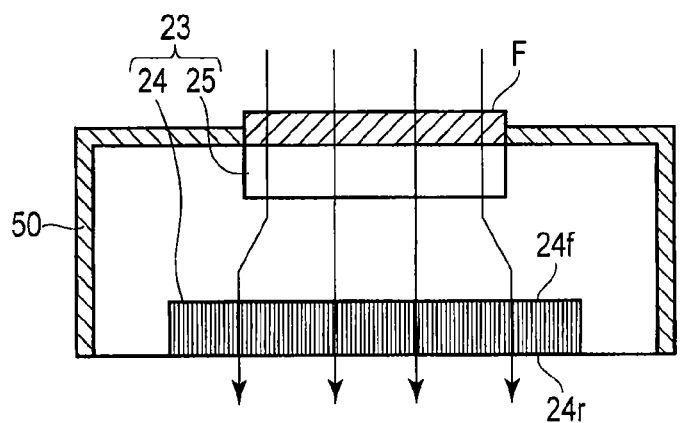
FIG. 5 is a schematic cross-sectional view showing a part of the cooling unit.

FIG. 5 is a schematic cross-sectional view showing a part of the cooling unit 20.

As shown in FIGS. 3 to 5, the heat exchanger 23 is provided across the circulation channel 30 to discharge the heat of the coolant 9 to the outside. The heat exchange 23 includes a radiator 24 and a fan unit 25.

The radiator 24 is provided across the circulation channel 30. The radiator 24 includes a plurality of heat dissipating pipes (not shown), which are connected between the conduits 21b and 21c and through which the coolant flows, and a plurality of heat dissipating fins (not shown) attached to the heat dissipating pipes. The radiator 24 can discharge the heat of the coolant 9 to the outside.

More specifically, the radiator 24 has a fin-tube structure (a radiator of a fin-tube type), and is substantially formed like a panel. The cross section of the heat dissipating pipes has a circular or flat shape. By virtue of the heat dissipating fins, the radiator 24 has a large surface area that is exposed to air.

The radiator 24 has a front surface 24f as an windward side and a rear surface 24r as a leeward side with respect to the flow of air through the radiator. For instance, when the flat fins are attached to the heat dissipating pipes such that they are perpendicular to the length of the heat dissipating pipes, the clearance between each pair of adjacent fins serves as an air passage. Further, when, for example, the tops of heat dissipating fins as corrugated panels are bonded to the side surfaces of flat heat dissipating pipes arranged at regular intervals, the clearance between each heat dissipating fin and the flat side surface of each heat dissipating pipe serves as an air passage.

The fan unit 25 is opposed to the front surface 24f of the radiator 24. The fan unit 25 can create the flow of air from the front surface 24f of the radiator 24 to the rear surface 24r. The fan unit 25 can discharge the air passing through the radiator 24 to the outside of the rotating frame 6 (frame member 7) through the opening 7a.

Thus, the heat exchanger 23 can discharge the heat of the coolant 9 to the outside. Further, since the air passing through the radiator 24 can be discharged to the outside of the rotating frame 6, increases in the temperature of the air within the rotating frame 6 can be suppressed.

An air filter F is provided on the air-intake side of the fan unit 25. The air filter F is used to filter out dust from the air passing therethrough. Thus, the fan unit 25 can create the flow of air passing through the air filter F and then through the radiator 24.

Since as described above, the air from which dust is eliminated passes through the radiator 24, deposition of dust in the radiator 24 (i.e., deposition of dust on the heat dissipating pipes and the heat dissipating fins) can be suppressed. This enables the air passages (the clearances between the heat dissipating pipes and the heat dissipating fins) of the radiator 24 to be hard to block. In the embodiment, the air passages of the radiator 24 are clearances of about 1 mm to 2 mm. Since reduction of the flow rate (quantity) of the air passing through the radiator 24 can be suppressed, reduction of the heat dissipating performance of the radiator 24 (i.e., the cooling performance of the cooling unit 20) can be suppressed.

The cooling unit 20 further comprises a casing 50 attached to the rotating frame 6. The casing 50 is secured to the inner wall of the frame member 7. The casing 50 is formed of, for example, a metal plate, and is designed to have a mechanical strength that can stand the centrifugal force applied by the rotation of the rotating frame 6.

The radiator 24 and the fan unit 25 are contained in the casing 50 and are unitized. The casing 50 has an opening through which the radiator 24 and the fan unit 25 are exposed to the outside. The air filter F is provided to substantially block the opening of the casing 50 through which the fan unit 25 are exposed. Namely, intrusion of dust into the casing 50 is suppressed.

The radiator 24 and the fan unit 25 are directly or indirectly secured to the rotating frame 6. In the embodiment, the radiator 24 and the fan unit 25 are indirectly secured to the inner wall of the frame member 7 via the casing 50.

As shown in FIGS. 3 and 4, the bellows mechanism 60 is directly or indirectly attached to the rotating frame 6. In the embodiment, the bellows mechanism 60 is directly attached to the frame member 7 independently of the housing 12, the circulation pump 22, the radiator 24 and the fan unit 25. The bellows mechanism 60 is attached to the circulation channel 30.

The bellows mechanism 60 comprises a case 61 having an opening 61a that air-tightly communicates with the conduit 21d. The bellows mechanism 60 further comprises a bellows 62 that serves as a diagram defining a first space 63 communicating with the opening 61a, and a second space 64. The case 61 also has an air hole 65 communicating with the second space 64. To permit air to pass through the air hole 65, the second space 64 is open to the atmosphere. The bellows 62 is liquid-tightly attached to the case 61. The bellows is retractable. In the embodiment, the bellows is formed of rubber. The bellows can absorb the volume variation (expansion and contraction) of the coolant 9 due to temperature variation. It is preferable to form the bellows of a material that exhibits impermissibility against gasses.

The plug 71 and the socket 72 form a coupler 70 as a detachable coupling member, and the plug 81 and the socket 82 form a coupler 80 as a detachable coupling member. The couplers 70 and 80 are each switchable between a coupled state (fixed state) where the plug and the socket are coupled, and a separation state where the plug and the socket are separated. In the coupled state, the couplers 70 and 80 are air-tightly and liquid-tightly coupled to each other. The couplers 70 and 80 each have a shut-off valve. In the separation states of the couplers 70 and 80, the plugs 71 and 81 and the sockets 72 and 82 have a structure capable of preventing a liquid (coolant 9) from leaking to the outside, and preventing outside air from entering the inside. When the couplers 70 and 80 are set in the separation states, the entire apparatus is separated into two systems, in which the X-ray tube assembly 10 and the cooling unit 20 are separated from each other.

When the X-ray tube assembly 10 is in the separation state, it has a structure in which the volume variation of the coolant 9 is hard to absorb. In view of this, the conduits 11a and 11b are formed of rubber hoses to impart a volume variation absorbing function to them. However, there is a case where the volume variation of the coolant 9 cannot sufficiently be absorbed. In this case, it is preferable to attach a bellows mechanism to the X-ray tube assembly 10 in the separation state.

A description will now be given of Examples 1 and 2 of the X-ray tube assembly 10 incorporated in the X-ray CT scanner of the first embodiment. Firstly, an X-ray tube assembly 10 as Example 1 will be described. FIG. 6 shows the cross section of X-ray tube assembly 10 of Example 1.

As shown in FIG. 6, the X-ray tube assembly 10 of Example 1 is a rotating anode X-ray tube assembly, and an X-ray tube 13 is a rotating anode X-ray tube. In addition to the X-ray tube 13, this X-ray tube assembly 10 comprises a stator coil 102 as a coil for generating a magnetic field. The X-ray tube 13 and the stator coil 102 are contained in a housing 12 (see FIG. 4).

The X-ray tube 13 comprises a fixed shaft 110 as a fixed member, a pipe 130, an anode target 150, a rotating unit 160, a liquid metal 170 as a lubricant, a cathode 180, and vacuum envelope 190. The X-ray tube 13 uses a dynamic-pressure sliding bearing.

The fixed shaft 110 extends along a rotation axis a2, whereby it is formed cylindrical about the rotation axis a2 with its one end portion blocked. The fixed shaft 110 has a bearing surface 110S as a side wall located separate from the one end portion. The fixed shaft 110 is formed of, for example, an alloy, such as an Fe or Mo (molybdenum) alloy. The interior of the fixed shaft 110 is filled with the coolant 9. The fixed shaft 110 has an internal channel for guiding the coolant 9, and an outlet 110b formed at the other end portion for discharging the coolant 9.

The pipe 130 is provided inside the fixed shaft 110, and forms a channel along with the fixed shaft. An end portion of the pipe 130 outwardly extends from the fixed shaft 110 through an opening 110a formed in the other end portion of the fixed shaft 110. The pipe 130 is tightly fitted in the opening 110a.

The pipe 130 has an inlet 130a for introducing the coolant 9, and an outlet 130b for discharging the coolant 9 into the fixed shaft 110. The inlet 130a is positioned outside the fixed shaft 110. The outlet 130b opposes the one end portion of the fixed shaft 110 with a gap defined therebetween.

The inlet 130a is directly connected to the conduit 11a, or indirectly connected thereto via a coupling member, and the outlet 110b is open to the interior of the housing 12. Alternatively, the inlet 130a may be open to the interior of the housing 12, and the outlet 110b may be directly connected to the conduit 11b, or indirectly connected thereto via a coupling member.

In the above-described structure, the coolant 9 is introduced from the outside of the X-ray tube 13 into the interior of the fixed shaft 110 through the inlet 130a thereof, and is discharged to the outside of the X-ray tube 13 from the outlet 110b through the space between the fixed shaft 110 and the pipe 130.

The anode target 150 comprises an anode 151, and a target layer 152 as a part of the outer surface of the anode. The anode 151 is formed like a disk, and provided coaxially with the fixed shaft 110. The anode 151 is formed of, for example, an Mo alloy, and has a cylindrical recess 151a formed about the rotation axis a2. The one end portion of the fixed shaft 110 is fitted in the recess 151a, with a clearance defined therebetween. The target layer 152 is formed of, for example, a W (tungsten) alloy and shaped annular. The surface of the target layer 152 is used as an electron colliding surface.

The rotating unit 160 is formed cylindrical and has a diameter greater than the fixed shaft 110. The rotating unit 160 is coaxial with the fixed shaft 110 and the anode target 150, and is shorter than the fixed shaft 110.

The rotating unit 160 is formed of, for example, Fe or Mo. More specifically, the rotating unit 160 comprises a cylindrical member 161, an annular member 162 formed integral with the cylindrical member 161 around the lateral periphery of one end portion of the cylindrical member 161, a sealing member 163 provided at the other end portion of the cylindrical member 161, and another cylindrical member 164.

The cylindrical member 161 surrounds the lateral periphery of the fixed shaft 110. The cylindrical member 161 has an inner surface that opposes the bearing surface 110S with a clearance therebetween and serves as a bearing surface 160S. One end portion of the rotating unit 160, i.e., one end portion of the cylindrical member 161 and the annular member 162, is coupled to the anode target 150. The rotating unit 160 is provided such that it is rotatable about the fixed shaft 110, along with the anode target 150.

The sealing member 163 is positioned on the opposite side of the annular member 162 (one end portion) with respect to the bearing surface 160S. The sealing member 163 is coupled to the other end portion of the cylindrical portion 161. The sealing member 163 is formed annular, and surrounds the lateral periphery of a lower portion of the fixed shaft 110 with a clearance defined therebetween. The cylindrical member 164 is coupled to the lateral periphery of the cylindrical member 161, is fixed to the cylindrical member 161, and is formed of, for example, Cu (copper).

A clearance between the one end portion of the fixed shaft 110 and the recess 151a and a clearance between the fixed shaft 110 (the bearing surface 110S) and the cylindrical member 161 (the bearing surface 160S) are filled with a liquid metal 170. The above-mentioned clearances all communicate with each other.

In the first embodiment, the liquid metal 170 is a gallium-indium-tin (GaInSn) alloy.

Along the orientation perpendicular to the rotation axis a2, the clearance between the sealing member 163 and the fixed shaft 110 is set to a value that enables rotation of the rotating unit 160 to be maintained, and leakage of the liquid metal 170 to be suppressed. In light of the above, the clearance is set to as small as 500 μm or less. Accordingly, the sealing member 163 functions as a labyrinth seal ring.

Further, the sealing member 163 has a plurality of receivers formed by depressing the inner surface thereof in the shape of a circular frame. The receivers will receive the liquid metal 170 in case it leaks from the clearances.

The cathode 180 is opposed to the target layer 152 of the anode target 150, with a gap interposed therebetween. The cathode 180 has a filament 181 for emitting electrons.

The vacuum envelope 190 contains the fixed shaft 110, the pipe 130, the anode target 150, the rotating unit 160, the liquid metal 170 and the cathode 180. The vacuum envelope 190 has an X-ray transmission window 190a and an opening 190b. The X-ray transmission window 190a is opposite to the target layer 152 at right angles to the rotation axis a2. The other end portion of the fixed shaft 110 extends to the outside of the vacuum envelope 190 through the opening 190b. The opening 190b is tightly fitted to the fixed shaft 110.

The cathode 180 is secured to the inner wall of the vacuum envelope 190. The vacuum envelope 190 is completely sealed and kept under a vacuum pressure.

The stator coil 102 is opposed to the lateral periphery of the rotating unit 160, more specifically, the lateral periphery of the cylindrical member 164 to surround the vacuum envelope 190. The stator coil 102 is formed annular.

The operation states of the X-ray tube 13 and the stator coil 102 will now be described. Since the stator coil 102 generates a magnetic field and applies it to the rotating unit 160 (in particular, the cylindrical member 164), the rotating unit 160 rotates. In accordance with this rotation, the anode target 150 also rotates. Further, a negative voltage (high voltage) is applied to the cathode 180 to set the anode target 150 to the ground potential.

As a result, a potential difference occurs between the cathode 180 and the anode target 150. In this state, when the cathode 180 generates electrons, these electrons are accelerated to bump against the target layer 152. Namely, the cathode 180 emits an electron beam to the target layer 152. When the electron beam has been applied to the target layer 152, the target layer 152 emits an X ray. The X ray is discharged to the outside of the vacuum envelope 190 via the X-ray transmission window 190a, and then to the outside of the housing 12.

As described above, the X-ray tube assembly 10 as Example 1 is constructed.

A description will then be given of an X-ray tube assembly 10 as Example 2. FIG. 7 is a cross-sectional view showing the X-ray tube assembly 10 as Example 2. FIG. 8 is another cross-sectional view showing the X-ray tube assembly 10 of FIG. 7. FIG. 9 is an enlarged sectional view showing a part of the X-ray tube assembly of FIGS. 7 and 8.

As shown in FIGS. 7 to 9, the X-ray tube assembly 10 is a stationary anode X-ray tube assembly, and the X-ray tube 13 is a stationary anode X-ray tube. The X-ray tube 13 comprises a vacuum envelope 231. The vacuum envelope 231 includes a vacuum container 232 and an insulating member 250. In this example, the insulating member 250 functions as a high-voltage insulating member. A cathode 236 is attached to the insulating member 250, and the insulating member 250 forms a part of the vacuum envelope 231.

Further, an anode target 235 forms a part of the vacuum envelope 231. The anode target 235 is slightly open to the outside of the vacuum envelope 231, and is formed like a vase having a swollen target surface 235b. The anode target 235, the cathode 236, a focusing electrode 209 and an acceleration electrode 208 are received in the vacuum envelope 231. A voltage supply line is connected to the anode target 235. The anode target 235 and the acceleration electrode 208 are set to the ground potential. The portion of the vacuum container 232 opposing the cathode 236 and the focusing electrode 209 is formed cylindrical. A negative high voltage is applied to the cathode 236. An adjusted negative high voltage is applied to the focusing electrode 209. The interior of the vacuum envelope 231 is kept in a vacuum state. A metal surface portion 234 is provided on the inner surface of the vacuum container 232 including the vacuum-side surface of an X-ray radiation window 231w, and is set to the ground potential.

The X-ray tube 13 comprises a tube portion 241 and an annular portion 242. The tube portion 241 is formed of a metal, and has its one end portion inserted in the anode target 235. The annular portion 242 is formed integral with the tube portion 241 as one body to enclose the one end portion of the tube portion 241. The annular portion 242 opposes the anode target 235 with a gap therebetween. The other end portion of the tube portion 241 forms a coolant inlet and is connected to the conduit 11a. The opening of the anode target 235 forms a coolant outlet along with the outer peripheral surface of the tube portion 241. As a result, the inside of the housing 12 is filled with the coolant 9. The housing 12 has an X-ray radiation window 12w opposing the X-ray radiation window 231w.

The housing 12 contains a deflecting unit 270. The deflecting unit 270 is a magnetic deflecting unit, and is located outside the vacuum container 232 to surround the path of an electron beam. The deflecting unit 270 is configured to deflect the electron beam emitted from the cathode 236 to shift the focal position of the beam onto the target surface 235b.

The X-ray tube assembly as Example 2 is constructed as described above.

The above-mentioned air filter F will be described.

The air filter F is formed of nonwoven fabric with a spatial volume ratio of 93% or more. The spatial volume ratio (%) means the volume ratio of a space contained in a unit volume.

Saran-lock and クレハロンロック (trademark) (kureharonrokku), for example, are included in the nonwoven fabric with a spatial volume ratio of 93% or more. Both materials form a three-dimensional structure in which resin fibers are irregularly tangled. These resin fibers are composed of polyvinylidene chloride as a main component.

Saran-lock is a three-dimensional nonwoven fabric produced by Asahi Kasei Home Products Corporation using saran (trademark) fiber. The three-dimensional structure is coated and bonded by latex containing vinylidene chloride as a main component, so as to bond the contact points of fibers. In saran-lock, some combinations of a thickness of 10 mm to 50 mm, a spatial volume ratio of 93% to 97% and a fiber diameter of 0.09 mm to 0.58 mm are standardized products.

Kureharonrokku is a three-dimensional nonwoven fabric produced by Musashino Giken Corporation. The three-dimensional structure is coated and bonded by latex containing polyvinylidene chloride as a main component, so as to bond the contact points of fibers. In kureharonrokku, some combinations of a thickness of 10 mm to 50 mm, a spatial volume ratio of 95% to 97% and a fiber diameter of 0.09 mm to 0.29 mm are standardized products.

Figure 24:
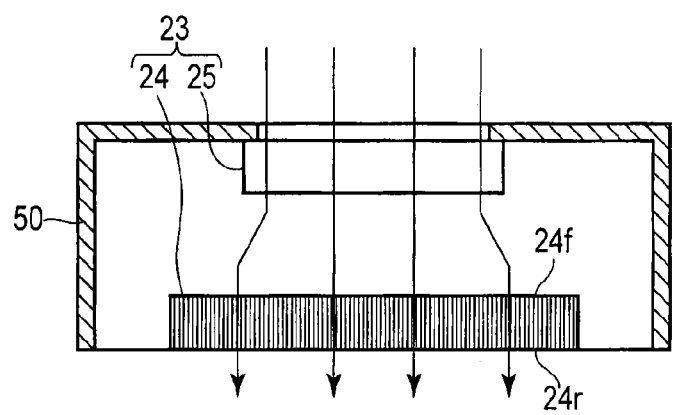
FIG. 24 is a schematic cross-sectional view showing a part of a cooling unit incorporated in the X-ray CT scanner of Comparative Example 1.

The fact that the air filter F can suppress reduction of the flow rate of the air passing through the radiator 24 will be clarified based on the result of the examination made by the inventors of the present application. FIG. 10 is a graph showing variations with elapsed days in the flow rates of the air passing through the radiators 24 of the X-ray CT scanner 1 of the first embodiment and that of Comparative Example 1. Namely, FIG. 10 shows attenuation rates of the air flow passing through the radiator 24. In this examination, kureharonrokku with a thickness of 10 mm, a spatial volume ratio of 96% and a fiber diameter of 0.23 mm was used. The X-ray CT scanner as Comparative Example 1 differs in structure from the X-ray CT scanner 1 of the embodiment only in that the former uses no air filter F, as is shown in FIG. 24.

The attenuation rate of the air flow passing through the radiator 24 was measured under the same conditions between the X-ray CT scanner 1 of the first embodiment and the X-ray CT scanner as Comparative Example 1. More specifically, the X-ray CT scanner 1 of the embodiment and the X-ray CT scanner as Comparative Example 1 were operated continuously in the same environment and at the same frequency. Further, when the X-ray CT scanner 1 was operated, only the cooling unit 20 (fan unit 25) was operated, and the X-ray tube assembly 10 was not operated. In the X-ray CT scanner 1 of the embodiment, no maintenance works were made on the radiator 24.

As shown in FIG. 10, the flow rates of the air passing through the radiator 24 are indicated by relative values. For instance, the flow rate of the air passing through the radiator 24 in the initial state of the X-ray CT scanner as Comparative Example 1 is set to 100%. Further, the limit of the flow rate, i.e., the lower limit of the flow rate that can maintain the heat dissipating performance of the radiator 24 (i.e., the cooling performance of the cooling unit 20), is set to 60%. In FIG. 10, line L1 indicates the examination result of the flow rate in the first embodiment, and line L2 indicates the examination result of the flow rate in Comparative Example 1.

In the first embodiment, as indicated by line L1, the flow rate of the air passing through the radiator 24 in the initial state is lower than in Comparative Example 1. This is because the air filter F slightly hinders the air flow. However, the flow rate in the initial state is still 95% that is much higher than 60%. The line L1 shows that the reduction rate of the air flow is low, namely, the flow rate is 89% even after 500 days elapse. This results from the fact that the air filter F removed dust from the air to thereby suppress deposition of dust in the radiator 24. From the above, it is understandable that in the embodiment, the reduction of the air flow passing through the radiator 24 was sufficiently suppressed. The dust deposited on the air filter F was all fiber dust (so called lint).

In contrast, as indicated by line L2, Comparative Example 1 exhibits a high air flow rate in the initial state, but exhibits a high reduction rate of air flow over time. Namely, after 250 days elapse, the air flow rate becomes lower than 60%. This is because the air passed through the radiator 24 without being filtered by the air filter F, and therefore deposition of dust in the radiator 24 continued. From the above, it is understandable that in Comparative Example 1, the reduction rate of the air flow could not be suppressed. The dust deposited on the radiator was fiber dust (so called lint) similar to the dust deposited on the air filter F in the embodiment.

Assume here that the reduction rate of flow of the air passing through the radiator 24 with respect to the operation time of the fan unit 25, where the air passes through the radiator 24 without passing through the air filter F, is k(0). In other words, k(0) is the reduction rate of flow of the air passing through the radiator 24 in Comparative Example 1.

Further, assume that the reduction rate of flow of the air passing through the radiator 24 with respect to the operation time of the fan unit 25 after passing through the air filter F is k(1). In other words, k(1) is the reduction rate of flow of the air passing through the radiator 24 in the embodiment.

In this case, k(0)>k(1). This is evident from lines L1 and L2 in FIG. 10.

k (k(0), k(1)) can be obtained from the following equations (1) and (2):

$$Qa = Q(0)(1-k(0)t) \quad \text{equation (1)}$$

$$Qb = Q(1)(1-k(1)t) \quad \text{equation (2)}$$

where Qa is the quantity of the air passing through the radiator 24 in Comparative Example 1, Q(0) is the initial value of the air passing through the radiator 24 in Comparative Example 1, Qb is the quantity of the air passing through the radiator 24 in the embodiment, and Q(1) is the initial value of the air passing through the radiator 24 in the embodiment. Further, t is time, k is a positive value, and Q(1)<Q(0).

Figure 11:
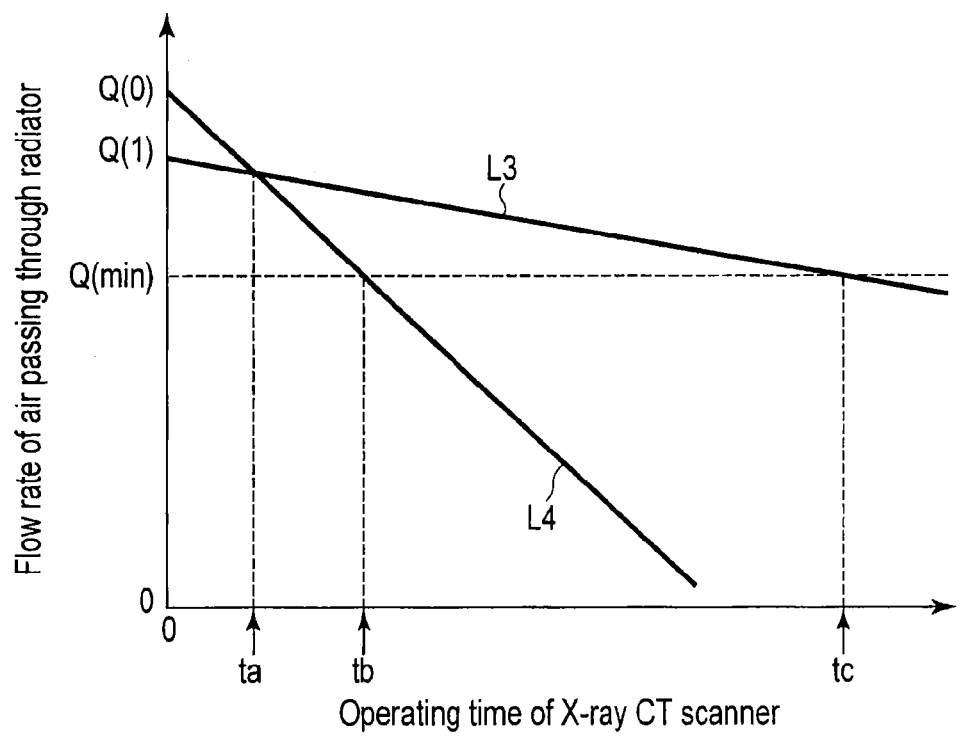
FIG. 11 is a graph showing variations with used hours in the flow rates of the air passing through the radiators of the X-ray CT scanner of the first embodiment and that of Comparative Example 1.

A more preferable condition for the air filter F will be clarified based on the examination result of the inventors of the present application. In this case, the condition will be clarified by examining variations in the quantity of the air passing through the radiator 24 between the embodiment and Comparative Example 1 under the same condition. FIG. 11 is a graph showing variations in the quantity of the air passing through the radiator with respect to the time of use of the X-ray CT scanners of the embodiment and Comparative Example 1.

As shown in FIG. 11, the quantity of the air passing through the radiator 24 is indicated relatively. In FIG. 11, line. L3 indicates the examination result of the flow rate (quantity) in the embodiment, and line L4 indicates the examination result of the flow rate (quantity) in Comparative Example 1.

Further, Q(min) indicates the lower limit of the air quantities Qa and Qb that can maintain the heat dissipating performance of the radiator 24 (i.e., the cooling performance of the cooling unit 20). Further, the time point where line L3 intersects line L4 (where Qa=Qb after the X-ray CT scanner is used for the same period of time) is supposed to be ta, the time point where line L4 intersects the dashed line indicating Q(min) (Qa=Q(min)) is supposed to be tb, and the time point where line L3 intersects the dashed line indicating Q(min) (Qb=Q(min)) is supposed to be tc.

ta, tb and tc are given by the following equations, based on the above-described equations (1) and (2):

$$ta=(Q(0)-Q(1))/(k(0) \cdot Q(0)-k(1) \cdot Q(1))$$

$$tb=(Q(0)-Q(\min))/(k(0) \cdot Q(0))$$

$$tc=(Q(1)-Q(\min))/(k(1) \cdot Q(1))$$

The condition to be satisfied by the air filter F is tb<tc.

Further, the more preferable condition to be satisfied by the air filter F is 2×tb<tc.

The X-ray CT scanner 1 of the first embodiment constructed as the above comprises the X-ray tube assembly 10, the cooling unit 20, the X-ray detector 40 and the rotating frame 6. The cooling unit 20 comprises the circulation pump 22, the radiator 24 and the fan unit 25. The rotating frame 6 has the frame member 7, to which the X-ray tube assembly 10, the circulation pump 22, the radiator 24, the fan unit 25 and the X-ray detector 40 are attached.

The fan unit 25 discharges the air flowing around the radiator 24 to the outside of the rotating frame 6 through the opening 7a.

If dust is deposited between the heat dissipating pipes and/or fins of the radiator 24 with lapse of used time of the X-ray CT scanner 1, it becomes difficult for the air to pass through the radiator 24, thereby degrading the cooling performance of the heat exchanger 23 to thereby reduce the cooling factor of the X-ray tube.

However, the X-ray CT scanner 1 comprises the air filter F capable of eliminating dust from the air. The fan unit 25 can create flow of the air passing through the radiator 24 after passing through the air filter F. Since thus, deposition of dust in the radiator 24 (i.e., deposition of dust on the heat dissipating pipes and the heat dissipating fins) can be suppressed, the air passages (the clearances between the heat dissipating pipes and between the heat dissipating fins) of the radiator 24 become hard to block. In contrast, the reduction of the flow rate (quantity) of the air passing through the air filter F due to the dust deposition thereon is small, the reduction of the flow rate (quantity) of the air passing through the radiator 24 can be suppressed. As a result, the reduction of the heat dissipating performance of the radiator 24 (i.e., the cooling performance of the cooling unit 20) can be suppressed.

As described above, a frequency of maintenance (cleaning) works for the radiator 24 can be reduced to thereby enhance the maintenance workability or realize a maintenance-free state.

By performing maintenance works so as not to degrade the function of the heat exchanger 23, overheating of the X-ray tube 13 can be suppressed. As a result, discharge that often occurs in the X-ray tube 13 can be minimized, which suppresses reduction of the life duration of the X-ray tube 13. In addition, in the X-ray tube assembly 10 as Example 1 (FIG. 6), excessive increase in the temperature of the bearing can be suppressed. Since thus, reaction between the liquid metal 170 and the bearing member can be suppressed, it is possible to prevent the bearing is non-rotatable.

Thus, the X-ray CT scanner 1 of the first embodiment is free from excessive reduction of the heat dissipating performance of the radiator 24.

A modification of the X-ray CT scanner 1 of the first embodiment will be described.

The cooling unit 20 may comprise ducts instead of the casing 50. The ducts are provided between the radiator 24 and the fan unit 25, and surround the respective peripheral edges of the radiator 24 and the fan unit 25. The ducts can prevent diffusion of the air flow created by the fan unit 25, and efficiently guide the air flow to the radiator 24. For instance, increases in the temperature of the air within the rotating frame 6 (the area surrounded by the rotating frame 6 and the casing 2) can be suppressed, whereby the cooling performance of the heat exchanger 23 and the stability of sensitivity of the X-ray detector 40 can be sustained.

Figure 12:
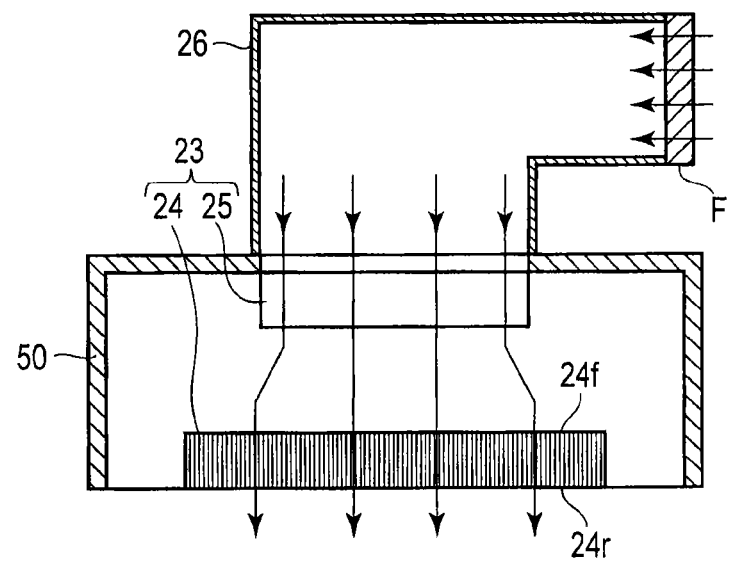
FIG. 12 is a schematic cross-sectional view showing a part of a cooling unit incorporated in an X-ray CT scanner according to a second embodiment.

An X-ray CT scanner according to a second embodiment will be described. In this embodiment, the same functional parts as in the above-described first embodiment are denoted by like reference numerals, and a detailed description is omitted. FIG. 12 is a schematic cross-sectional view showing a part of the cooling unit 20 incorporated in the X-ray CT scanner 1 of the second embodiment.

As shown in FIG. 12, the air filter F may be indirectly attached to the casing 50. The cooling unit 20 further comprises a duct 26.

The air filter F is fitted in the air inlet opening (windward-side opening) of the duct 26. The duct 26 is attached to the casing 50 such that the air outlet opening (leeward-side opening) of the duct 26 communicates with the opening of the casing 50 in which the fan unit 25 is fitted. The shape of the duct 26 is not limited but may be modified in various ways. The duct 26 guides, to the fan unit 25, the air having passed through the air filter F. As a result, only the air without dust is guided to the radiator 24. Thus, also when the duct 26 is used, deposition of dust in the radiator 24 can be suppressed.

As described above, the X-ray CT scanner 1 of the second embodiment additionally comprises the duct 26. The fan unit 25 can create an air flow that passes through the air filter F, then passes along the duct 26 and passes through the radiator 24. Also in the second embodiment, deposition of dust in the radiator 24 (i.e., deposition of dust on the heat dissipating pipes and the heat dissipating fins) can be suppressed, thereby suppressing reduction of the heat dissipation performance of the radiator 24 (i.e., the cooling performance of the cooling unit 20).

The second embodiment also provides the same advantages as those of the first embodiment.

As described above, the second embodiment provides an X-ray CT scanner 1 capable of suppressing reduction of the heat dissipation performance of the radiator 24.

Figure 13:
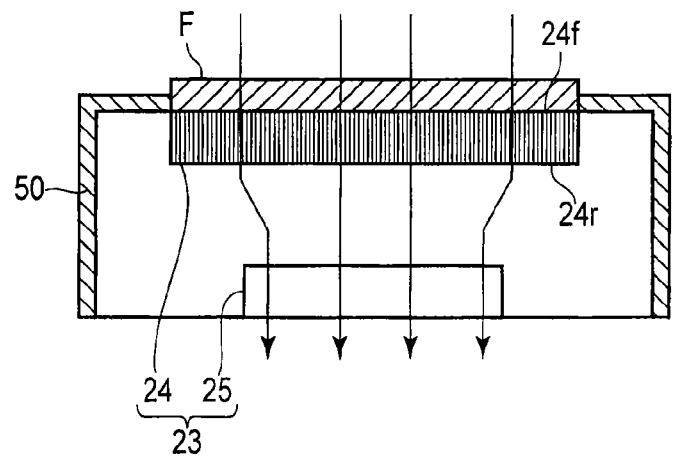
FIG. 13 is a schematic cross-sectional view showing a part of a cooling unit incorporated in an X-ray CT scanner according to a third embodiment.

An X-ray CT scanner according to a third embodiment will be described. In this embodiment, the same functional parts as in the above-described first embodiment are denoted by like reference numerals, and a detailed description is omitted. FIG. 13 is a schematic cross-sectional view showing a part of the cooling unit 20 incorporated in the X-ray CT scanner 1 of the third embodiment.

As shown in FIG. 13, the distance between the rotation axis a1 and the fan unit 25 is longer than that between the rotation axis a1 and the radiator 24 (see FIG. 3). The air filter F is fitted in the opening of the casing 50, and the windward side (24f) of the radiator 24 with respect to the air flow is located leeward of the air filter F.

In the X-ray CT scanner 1 of the third embodiment constructed as the above, the windward side of the radiator 24 with respect to the air flow extends to the outside of the casing 50. Also in this case, the fan unit 25 can create an air flow passing through the radiator 24 after passing through the air filter F. Also in the third embodiment, deposition of dust in the radiator 24 (i.e., deposition of dust on the heat dissipating pipes and the heat dissipating fins) can be suppressed, thereby suppressing reduction of the heat dissipation performance of the radiator 24 (i.e., the cooling performance of the cooling unit 20).

In the above-described embodiments, kureharonrokku with a thickness of 10 mm, a spatial volume ratio of 96% and a fiber diameter of 0.23 mm is used as the air filter F. However, even when the thickness was set greater than 10 mm with the structure unchanged, there was little difference in variation of air permeability with elapse of time, although the air permeability in the initial stage was reduced. Further, variation in the air permeability with lapse of time was smaller when the spatial volume ratio or the fiber diameter was greater. Furthermore, when standardized products of saran-lock and kureharonrokku, which were obtained as combinations of a thickness of 10 mm to 50 mm, a spatial volume ratio of 90% to 97% and a fiber diameter of 0.23 mm to 0.58 mm, were used, it was confirmed that deposition of dust in the radiator 24 (i.e., deposition of dust on the heat dissipating pipes and heat dissipating pipes fins) can be suppressed, thereby suppressing reduction of the heat dissipation performance of the radiator 24 (i.e., the cooling performance of the cooling unit 20).

The above-described air filter is not generally used for a fin-tube type radiator. The inventors of the present application experimentally used for the first time for the fin-tube type radiator. The above-mentioned advantage was an unexpected result even to the inventors, and is not a generally known advantage.

The conventional air filters used for an X-ray tube cooling system have an opening formed using a fine mesh material, like a sponge filter of a foam material as disclosed in Jpn. Pat. Appln. KOKAI Publication No. 2007-514287. Since air flows through the small spaces in the sponge filter, dust will be gradually deposited on the filter with lapse of time to thereby block the spaces. This may well result in reduction of air permeability at an early date.

Figure 14:
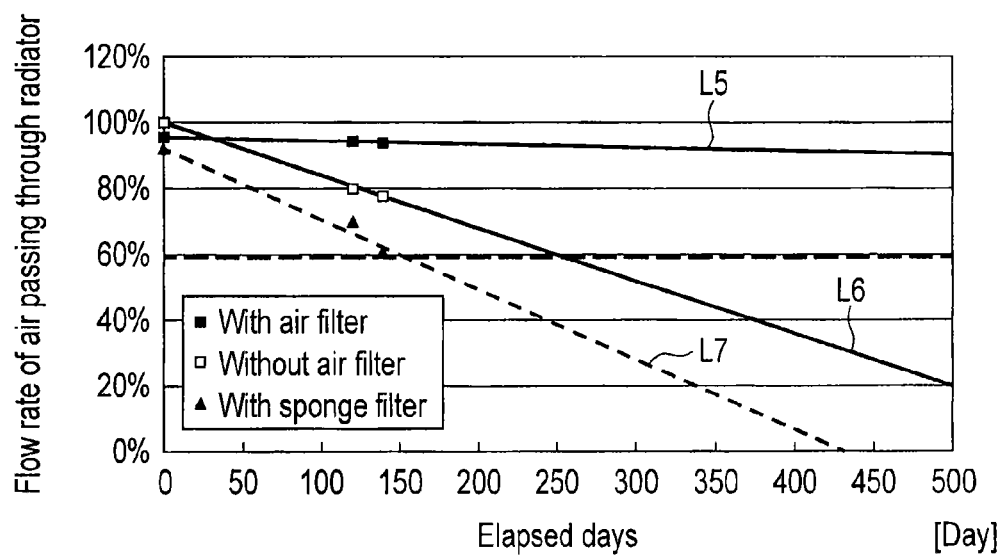
FIG. 14 is a graph showing variations with elapsed days in the flow rates of the air passing through the radiators of the X-ray CT scanner of the third embodiment and those of Comparative Examples 2 and 3.
Figure 25:
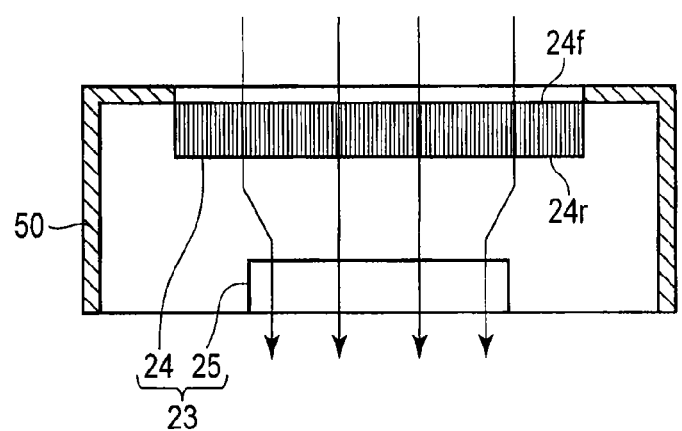
FIG. 25 is a schematic cross-sectional view showing a part of a cooling unit incorporated in the X-ray CT scanner of Comparative Example 2.

The difference between the above-described air filter F and the conventional air filter will be described based on the result of the examination made by the inventors of the present application. FIG. 14 is a graph showing variations with elapsed days in the flow rates of the air passing through the radiators 24 of the X-ray CT scanner 1 of the third embodiment and those of Comparative Examples 2 and 3. Namely, FIG. 14 shows the attenuation rate of the air flow passing through the radiator 24. As shown in FIG. 25, the X-ray CT scanner as Comparative Example 2 differs from the X-ray CT scanner 1 of the third embodiment only in that the former employs no air filter F. Further, as shown in FIG. 26, the X-ray CT scanner as Comparative Example 3 differs from the X-ray CT scanner 1 of the third embodiment only in that the former employs a sponge filter S instead of the air filter F.

When the attenuation rate of the air flow passing through the radiator 24 was examined, the X-ray CT scanner 1 of the third embodiment and the X-ray CT scanners as Comparative Examples 2 and 3 were subjected to the examination under the same conditions. For instance, the X-ray CT scanner 1 of the third embodiment and the X-ray CT scanners as Comparative Examples 2 and 3 were operated continuously in the same environment and at the same frequency. Further, when the X-ray CT scanner 1 was operated, only the cooling unit 20 (fan unit 25) was operated, and the X-ray tube assembly 10 was not operated. In the X-ray CT scanner 1 of the third embodiment and the X-ray CT scanners of the Comparative Examples 2 and 3, no maintenance works were made on the radiator 24.

As shown in FIG. 14, the flow rates of the air passing through the radiator 24 are indicated by relative values. For instance, the flow rate of the air passing through the radiator 24 in the initial state of the X-ray CT scanner as Comparative Example 2 is set to 100%. Further, the limit of the flow rate, i.e., the lower limit of the flow rate that can maintain the heat dissipating performance of the radiator 24 (i.e., the cooling performance of the cooling unit 20), is set to 60%. In FIG. 14, line L5 indicates the examination result of the flow rate in the third embodiment, line L6 indicates the examination result of the flow rate in Comparative Example 2, and line L7 indicates the examination result of the flow rate in Comparative Example 3.

Regarding the first embodiment and Comparative Example 3, as indicated by lines L5 and L7, the flow rates of the air passing through the radiator 24 in the initial state are lower than in Comparative Example 2. This is because the air filter F or the sponge filter S slightly hinders the air flow. However, their flow rates in the initial state are much higher than 60% (95% in the third embodiment, and 92% in Comparative Example 3). Further, the flow rate in the third embodiment is 89% even after 500 days elapse. This results from the fact that the air filter F removed dust from the air to thereby suppress deposition of dust in the radiator 24. From the above, it is understandable that in the third embodiment, the reduction of the air flow passing through the radiator 24 was sufficiently suppressed.

In contrast, as indicated by lines L6 and L7, Comparative Examples 2 and 3 exhibit high reduction rates of air flow. Line L6 indicates that after 250 days elapse, the air flow rate becomes lower than 60%. Similarly, line L7 indicates that after 150 days elapse, the air flow rate becomes lower than 60%. From this, it is understandable that in Comparative Examples 2 and 3, reduction of the air flow passing through the radiator 24 could not be suppressed.

Further, in the third embodiment, simply by detaching a part of the housing 2 and removing the air filter F, the radiator 24 can be cleaned from the space on the inner wall side of the frame member 7 to thereby remove the dust deposited in the radiator 24. Namely, the radiator 24 can be cleaned without detaching the cooling unit 20 from the rotating frame 6, or without further detaching the X-ray tube assembly 10 from the cooling unit 20. This can reduce the time required for cleaning (maintenance work).

The third embodiment also provides other advantages similar to those of the first embodiment.

As described above, the third embodiment provides an X-ray CT scanner 1 wherein reduction in the heat dissipating performance of the radiator 24 is suppressed.

An X-ray CT scanner according to a fourth embodiment will be described. In this embodiment, the same functional parts as in the above-described third embodiment are denoted by like reference numerals, and a detailed description is omitted. FIG. 15 is a schematic cross-sectional view showing a part of the cooling unit 20 incorporated in the X-ray CT scanner 1 of the fourth embodiment.

As shown in FIG. 15, the air filter F may be indirectly attached to the housing 50. Namely, the cooling unit 20 further comprises a duct 26.

The air filter F is fitted in the air inlet opening (windward-side opening) of the duct 26. The duct 26 is attached to the casing 50 such that the air outlet opening (leeward-side opening) of the duct 26 communicates with the opening of the casing 50 through which the radiator 24 is exposed. The shape of the duct 26 is not limited but may be modified in various ways. The duct 26 guides, to the radiator 24, the air having passed through the air filter F. As a result, only the air without dust is guided to the radiator 24. Thus, also when the duct 26 is used, deposition of dust in the radiator 24 can be suppressed.

As described above, the X-ray CT scanner 1 of the fourth embodiment additionally comprises the duct 26. The fan unit 25 can create an air flow that passes through the air filter F, then passes along the duct 26 and passes through the radiator 24. Also in the fourth embodiment, deposition of dust in the radiator 24 (i.e., deposition of dust on the heat dissipating pipes and the heat dissipating fins) can be suppressed, thereby suppressing reduction of the heat dissipation performance of the radiator 24 (i.e., the cooling performance of the cooling unit 20).

The fourth embodiment also provides the same advantages as those of the third embodiment.

As described above, the fourth embodiment provides an X-ray CT scanner 1 capable of suppressing reduction of the heat dissipation performance of the radiator 24.

An X-ray CT scanner according to a fifth embodiment will be described. In this embodiment, the same functional parts as in the above-described first embodiment are denoted by like reference numerals, and a detailed description is omitted. FIG. 16 is a schematic cross-sectional view showing a part of the cooling unit 20 incorporated in the X-ray CT scanner 1 of the fifth embodiment. FIG. 16 does not show the radiator 24 and the fan unit 25.

As shown in FIG. 16, the X-ray CT scanner 1 further comprises a frame member 91, a holding member 92 and fixing member. The fixing member may include a screw 93 as a fastening member.

A frame member 91 is formed in accordance with the shape of the air filter F. The frame member 91 encloses the periphery of the air filter F to support the same. Thus, the air filter F is always fixed by the frame member 91.

The holding member 92 is fixed to the housing 50. The holding member 92 is formed to be able to receive one side portion of the frame member 91. To reduce the jounce of the frame member 91, shape and size of the receiving portion of the holding member 92 may be substantially the same in shape and size of the frame member 91. By holding the one side of the frame member 91, the holding member 92 indirectly holds the air filter F. The holding member 92 can be also used to position the air filter F and the frame member 91.

The screw 93 fixes another side of the frame member 91 to indirectly fix the position of the air filter F. Thus, the screw 93 is screwed in a screw hole formed in the housing 50 through a through hole formed in the frame member 91.

When the air filter F is attached to the housing 50, firstly, the frame member 91 formed integral with the air filter F is fitted in the receiving portion of the holding member 92. After that, the screw 93 is screwed into the screw hole of the housing 50 through the through hole of the frame member 91.

When the air filter F is detached from the housing 50, firstly, the screw 93 is loosened, and then, the frame member 91 formed integral with the air filter F is pulled out of the receiving portion of the holding member 92.

As described above, the air filter F can be mounted on the outer surface of the housing 50 such that it is detachable along with the frame member 91.

The X-ray CT scanner 1 and the method of mounting the air filter F, according to the fifth embodiment, the X-ray CT scanner 1 comprises the air filter F. Therefore, the same advantageous effects as in the first embodiment can be obtained.

As described above, the fifth embodiment provides the X-ray CT scanner 1 capable of suppressing reduction of the heat dissipation performance of the radiator 24.

Further, the X-ray CT scanner 1 of the fifth embodiment further comprises the frame member 91, the holding member 92 and the screw 93, and the air filter F and the frame member 91 are formed integral as one body. Therefore, the air filter F can be easily attached and detached.

An X-ray CT scanner according to a modification of the fifth embodiment will be described.

FIG. 17 is a schematic cross-sectional view showing a part of an X-ray CT scanner according to a modification of the fifth embodiment, more specifically, showing an example of installation of the air filter F. FIG. 17 does not show the radiator 24 and the fan unit 25.

As shown in FIG. 17, the X-ray CT scanner 1 of this modification does not incorporate the holding member 92. Instead, a plurality of through holes are formed in a plurality of side portions of the frame member 91. Through these through holes, screws 93 are screwed into corresponding screw holes formed in the housing 50.

FIG. 18 is a schematic cross-sectional view showing a part of an X-ray CT scanner according to another modification of the fifth embodiment, more specifically, showing an example of installation of the air filter F. FIG. 18 does not show the radiator 24 and the fan unit 25.

As shown in FIG. 18, the X-ray CT scanner 1 employs a magnet 94 as a stationary member, instead of the holding member 92 and the screw 93. The magnet 94 is located between the housing 50 and the frame member 91. The magnet 94 is attached at least to the housing 50 or the frame member 91. In this case, the frame member 91 can be secured to the housing 50 by the magnetic force. It is a matter of course that the frame member 91 and the housing 50 are formed of a material, such as a metal, that can be attracted by the magnetic force.

The fixing member is not limited to the magnet 94, but may be modified to various materials, such as a hook-and-loop fastener and a double-sided tape.

FIG. 19 is a schematic cross-sectional view showing a part of an X-ray CT scanner according to yet another modification of the fifth embodiment, more specifically, showing an example of installation of the air filter F. FIG. 19 does not show the radiator 24 and the fan unit 25. FIG. 20 is an enlarged cross-sectional view showing a part of the cooling unit 20 of FIG. 19, more specifically, showing a frame member and projections.

As shown in FIGS. 19 and 20, the air filter F is installed using a frame member 91 of a set-in type. The frame member 91 is formed of an elastically deformable material. The frame member 91 has an opening 910 as a set-in hole opposing the housing 50. Notches 91r are formed in the inner surface of the frame member 91 that defines the opening 91o.

Projecting portions 95 extend from the portions of the housing 50 opposing the opening 91o. The projecting portions 95 have projections 95p projecting perpendicular to the heights of the projecting portions 95 from the housing 50. The projections 95p oppose the notches 91r. When the projections 95p are fitted in the notches 91r, the frame member 91 is fixed in position.

When the air filter F is attached to the housing 50, the opening 91O of the frame member 91, which is integral with the air filter F, is fitted onto the projecting portions 95.

When the air filter F is detached from the housing 50, the frame member 91 is pulled away from the projecting portions 95.

As described above, the air filter F can be detachably mounted on the outer surface of the housing 50, along with the frame member 91.

FIG. 21 is a schematic cross-sectional view showing a part of an X-ray CT scanner according to a further modification of the fifth embodiment, more specifically, showing an example of installation of the air filter. FIG. 21 does not show the radiator 24 and the fan unit 25. FIG. 22 is a top view of the air filter F and the frame member 91 shown in FIG. 21.

As shown in FIGS. 21 and 22, the air filter F is not secured to the frame member 91. The frame member 91 is formed integral with or attached to the housing 50, and has a frame-shaped receiver for receiving the peripheral portion of the air filter F.

When the air filter F is mounted, it is bent and fitted into the receiver of the frame member 91.

As described above, the air filter F can be detachably attached singly.

Figure 23:
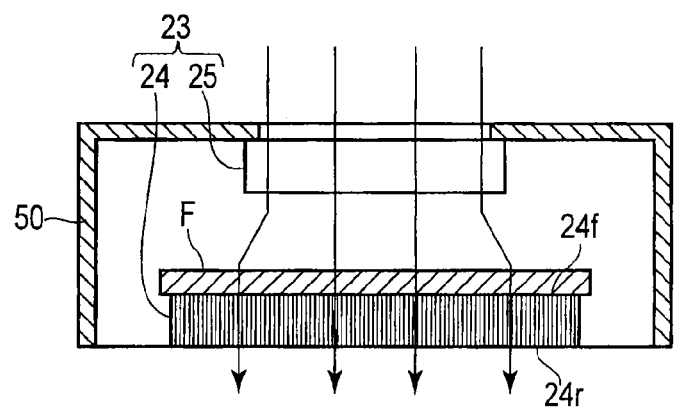
FIG. 23 is a schematic cross-sectional view showing a part of a cooling unit incorporated in an X-ray CT scanner according to a sixth embodiment.

An X-ray CT scanner according to a sixth embodiment will be described. In this embodiment, the same functional parts as in the above-described first embodiment are denoted by like reference numerals, and a detailed description is omitted. FIG. 23 is a schematic cross-sectional view showing a part of the cooling unit 20 incorporated in the X-ray CT scanner 1 of the sixth embodiment.

As shown in FIG. 23, the air filter F is contained in the housing 50. The air filter F is provided on the windward-side surface of the radiator 24.

As described above, the X-ray CT scanner 1 of the sixth embodiment comprises an air filter F provided on the windward-side surface of the radiator 24. Also in this case, the fan unit 25 can create the flow of air passing through the air filter F and then through the radiator 24. Also in the sixth embodiment, deposition of dust in the radiator 24 (i.e., deposition of dust on the heat dissipating pipes and the heat dissipating fins) can be suppressed, whereby the reduction of the heat dissipating performance of the radiator 24 (i.e., the cooling performance of the cooling unit 20) can be suppressed. As a result, a frequency of the maintenance (cleaning) works of the radiator 24 can be reduced, or a maintenance-free state can be realized.

Thus, an X-ray CT scanner 1, in which reduction of the heat dissipating performance of the radiator 24 is suppressed, can be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For instance, the above-described embodiments are not limited to X-ray CT scanners, but are also applicable to various types of X-ray apparatuses that use the X-ray tube assembly 10 including the cooling unit 20.

What is claimed is:

1. An X-ray tube assembly comprising:
   a housing;
   an X-ray tube housed in the housing and including a cathode configured to emit an electron beam, an anode target configured to discharge an X ray when the electron beam is applied to the anode target, and a vacuum envelope containing the cathode and the anode target;
   a coolant to which at least a part of heat generated by the X-ray tube is transferred;
   a circulation channel through which the coolant is circulated;
   a circulation pump provided across the circulation channel and configured to circulate the coolant;
   a radiator of a fin-tube type provided across the circulation channel and configured to discharge the heat of the coolant to an outside;
   an air filter formed of a three-dimensional nonwoven fabric and configured to permit air to pass therethrough to eliminate dust from the air, the three-dimensional nonwoven fabric being formed of irregularly tangled resin fibers and providing a three-dimensional structure having a spatial volume ratio of not less than 93%; and
   a fan unit configured to create a flow of air passing through the radiator after passing through the air filter.

2. The X-ray tube assembly of claim 1, wherein
   each resin fiber has a thickness of not less than 10 mm; and
   the resin fabric has a diameter of 0.23 to 0.58 mm.

3. The X-ray tube assembly of claim 1, wherein
   the resin fibers are composed of polyvinylidene chloride as a main component; and
   the three-dimensional structure is bonded and coated with latex containing polyvinylidene chloride as a main component.

4. The X-ray tube assembly of claim 1, further comprising a duct provided between the radiator and the fan unit and configured to guide a flow of the air between the radiator and the fan unit.

5. The X-ray tube assembly of claim 1, further comprising a bellows mechanism provided across the circulation channel and configured to absorb a change in a volume of the coolant due to a change in temperature.

6. The X-ray tube assembly of claim 1, further comprising a casing,
   wherein at least the fan unit and the radiator are contained in the casing and are unitized.

7. The X-ray tube assembly of claim 1, wherein $k(0)>k(1)$ is established, where $k(0)$ indicates a reduction rate of a quantity of air with respect to an operation time of the fan unit assuming that the air passes through the radiator without passing through the air filter, and $k(1)$ indicates a reduction rate of the quantity of the air with respect to the operation time of the fan unit when the air passes through the radiator after passing through the air filter.

8. An X-ray computerized tomography scanner comprising:
   an X-ray tube assembly including:
      a housing;
      an X-ray tube housed in the housing and including a cathode configured to emit an electron beam, an anode target configured to discharge an X ray when the electron beam is applied to the anode target, and a vacuum envelope containing the cathode and the anode target;

a coolant to which at least a part of heat generated by the X-ray tube is transferred;

a circulation channel through which the coolant is circulated;

a circulation pump provided across the circulation channel and configured to circulate the coolant;

a radiator of a fin-tube type provided across the circulation channel and configured to discharge the heat of the coolant to an outside;

an air filter formed of a three-dimensional nonwoven fabric and configured to permit air to pass therethrough to eliminate dust from the air, the three-dimensional nonwoven fabric being formed of irregularly tangled resin fibers and providing a three-dimensional structure having a spatial volume ratio of not less than 93%; and a fan unit configured to create a flow of air passing through the radiator after passing through the air filter; and an X-ray detector configured to detect the X ray; and a rotating frame to which the X-ray tube assembly and the X-ray detector are attached.

9. The X-ray computerized tomography scanner of claim 8, wherein the air filter has a thickness of not less than 10 mm; and each resin fiber has a diameter of 0.23 to 0.58 mm.

10. The X-ray computerized tomography scanner of claim 8, wherein the resin fibers are composed of polyvinylidene chloride as a main component; and the three-dimensional structure is bonded and coated with latex containing polyvinylidene chloride as a main component.

11. The X-ray computerized tomography scanner of claim 8, further comprising a duct provided between the radiator and the fan unit and configured to guide a flow of the air between the radiator and the fan unit.

12. The X-ray computerized tomography scanner of claim 8, further comprising a bellows mechanism provided across the circulation channel and configured to absorb a change in a volume of the coolant due to a change in temperature.

13. The X-ray computerized tomography scanner of claim 8, further comprising a casing, wherein at least the fan unit and the radiator are contained in the casing and are unitized.

14. The X-ray computerized tomography scanner of claim 8, wherein $k(0)>k(1)$ is established, where $k(0)$ indicates a reduction rate of a quantity of air with respect to an operation time of the fan unit assuming that the air passes through the radiator without passing through the air filter, and $k(1)$ indicates a reduction rate of the quantity of the air with respect to the operation time of the fan unit when the air passes through the radiator after passing through the air filter.

15. The X-ray computerized tomography scanner of claim 8, wherein the fan unit is attached to the rotating frame independently of the radiator and the circulation pump.

* * * * *